US00PP37496P2

(12) United States Plant Patent
Smith

(10) Patent No.: US PP37,496 P2
(45) Date of Patent: Jun. 30, 2026

(54) ***SPIRAEA* PLANT NAMED 'WALPLUCAR'**

(50) Latin Name: ***Spiraea* x *bumalda***
Varietal Denomination: WALPLUCAR

(71) Applicant: WALBERTON PLANTS LIMITED, Arundel (GB)

(72) Inventor: Dawn Smith, Arundel (GB)

(73) Assignee: Walberton Plants Ltd, Walberton (GB)

( * ) Notice: Subject to any disclaimer, the term of this patent is extended or adjusted under 35 U.S.C. 154(b) by 0 days.

(21) Appl. No.: 19/239,543

(22) Filed: Jun. 16, 2025

(51) Int. Cl.
*A01H 5/02* (2018.01)
*A01H 6/74* (2018.01)

(52) U.S. Cl.
USPC ..... Plt./226

(58) Field of Classification Search
USPC ..... Plt./226
CPC ... A01H 5/02; A01H 5/12; A01H 5/00; A01H 6/74
See application file for complete search history.

(56) References Cited

PUBLICATIONS

HTA Show Guide 2024 retrieved on Sep. 23, 2025 at https://hta.org.uk/media/zjkhvcm3/hta-19578-show-guide-2024-nps-6-lowres.pdf, pp. 1-3, 28-29 (3 pp. total) (Year: 2024).*
HTA Spiraea Walberton's Plum Carpet wins the Visitor Vote at the HTA National Plant Show, retrieved on Sep. 23, 2025 at https://hta.org.uk/news/spiraea-walberton-s-plum-carpet-wins-the-visitor-vote-at-the-hta-national-plant-show, 3 pp. (Year: 2024).*
Plant Haven International, Inc. Spiraea Walberton's Plum Carpet, retrieved on Sep. 23, 2025 at https://planthaven.com/plant/spiraea-walbertons-plum-carpet/, 3 pp. (Year: 2025).*
Plants for Europe, Four Spectacular New Plant Varieties Launching this summer 2024, retrieved on Sep. 23, 2025 at https://www.plantsforeurope.com/four-new-plant-varieties/, 8 pp. (Year: 2024).*

* cited by examiner

*Primary Examiner* — June Hwu
(74) *Attorney, Agent, or Firm* — Weatherly IP Solutions, LLC; James M. Weatherly

(57) ABSTRACT

A new *Spiraea* plant particularly distinguished by having deep plum red glossy rugose juvenile spring foliage with deeply sulcate veins; and right pink-red inflorescences.

3 Drawing Sheets

Genus and species: Spiraea x *bumalda*.
Variety denomination: 'WALPLUCAR'.

BACKGROUND

The present invention comprises a new and distinct variety of *Spiraea*, botanically known as *Spiraea x bumalda* and hereinafter referred to by the variety name 'WALPLUCAR'. 'WALPLUCAR' originated from a spontaneous open pollination in a plant nursery in Walberton, West Sussex, United Kingdom between the Spiraea 'WALPLUM' (U.S. Plant Pat. No. 29,405) and *Spiraea* 'WALBUMA' (U.S. Plant Pat. No. 9,363).

A single plant seedling was discovered in June 2017 in Walberton, West Sussex, United Kingdom and subsequently named 'WALPLUCAR'. In August 2017, 'WALPLUCAR' was first vegetatively propagated by internodal cuttings in Walberton, West Sussex, United Kingdom. 'WALPLUCAR' was found to reproduce true to type in successive generations of asexual propagation via stem cuttings in Walberton, West Sussex, United Kingdom.

SUMMARY OF THE INVENTION

The following traits have been repeatedly observed and represent the distinguishing characteristics of the new *Spiraea* named 'WALPLUCAR'. These traits in combination distinguish 'WALPLUCAR' from all other existing varieties of *Spiraea* known to the inventor. 'WALPLUCAR' has not been tested under all possible conditions and phenotypic differences may be observed with variations in environmental, climatic, and cultural conditions, however, without any variance in genotype.

Deep plum red glossy rugose juvenile spring foliage with deeply sulcate veins; and Bright pink-red inflorescences.

BRIEF DESCRIPTION OF THE PHOTOGRAPHS

The accompanying color photographs FIG. 1, FIG. 2, and FIG. 3 illustrate the overall appearance of the new *Spiraea* cultivar 'WALPLUCAR' showing the colors as true as it is reasonably possible to obtain in colored reproductions of this type. Colors in the photograph may differ from the color values cited in the detailed botanical description, which accurately describe the actual colors of the new variety 'WALPLUCAR'.

Figure 1:
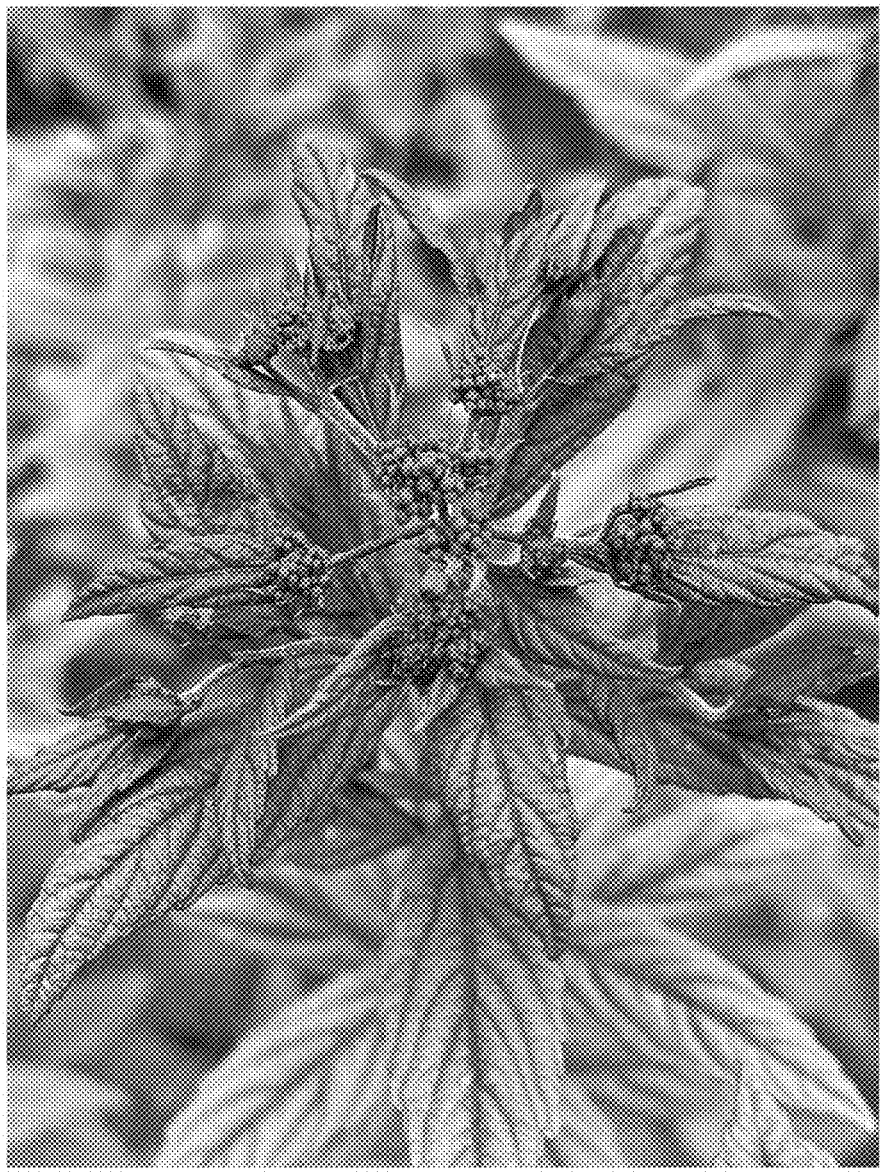
FIG. 1 illustrates 'WALPLUCAR' with glossy new spring foliage and inflorescence buds. The photo was taken on a one year old plant on May 18, 2024 in Walberton, West Sussex, United Kingdom.
Figure 2:
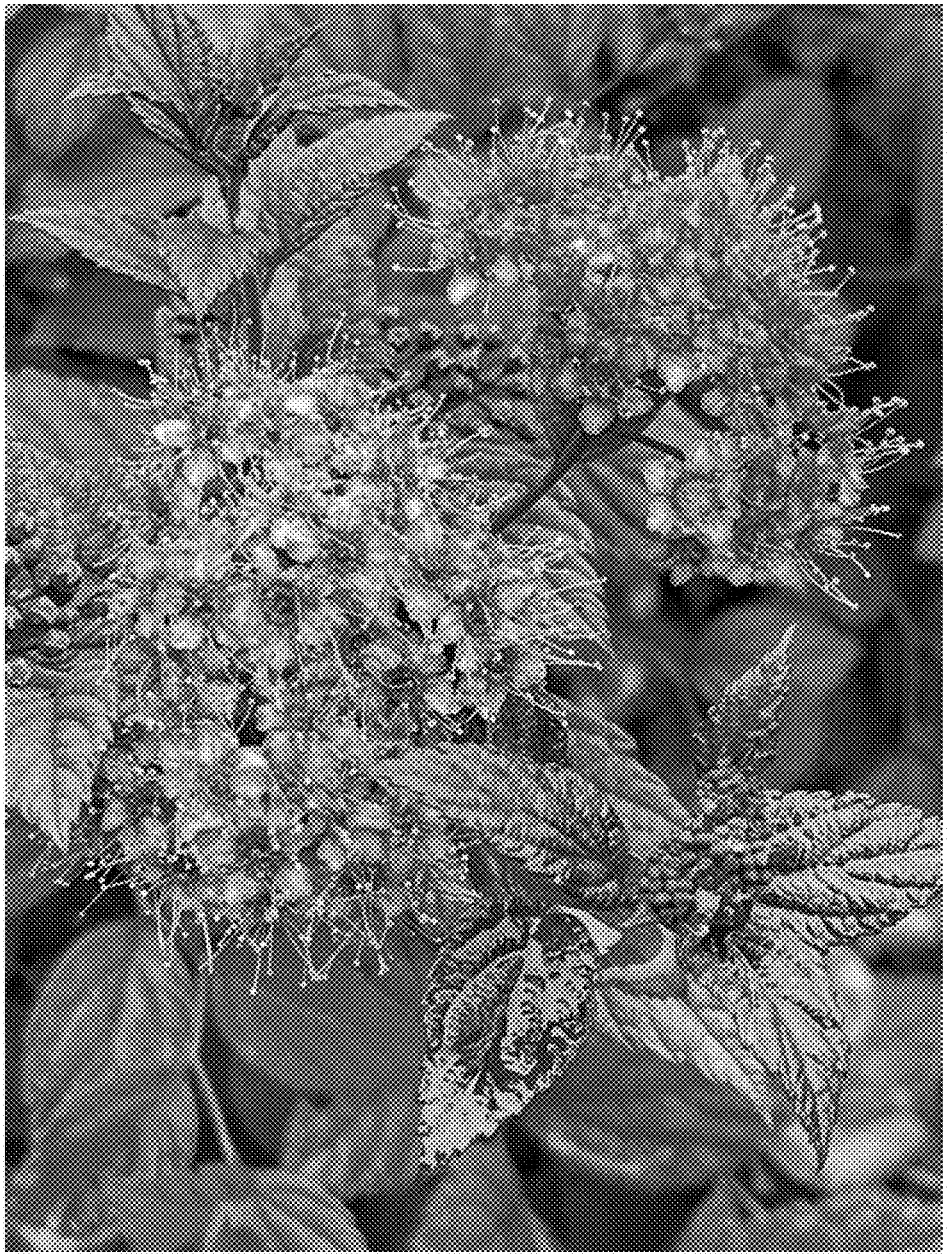
FIG. 2 illustrates a one-year-old plant of 'WALPLUCAR' with close up on flowers. The photo was taken on a one year old plant on May 18, 2024 in Walberton, West Sussex, United Kingdom.
Figure 3:
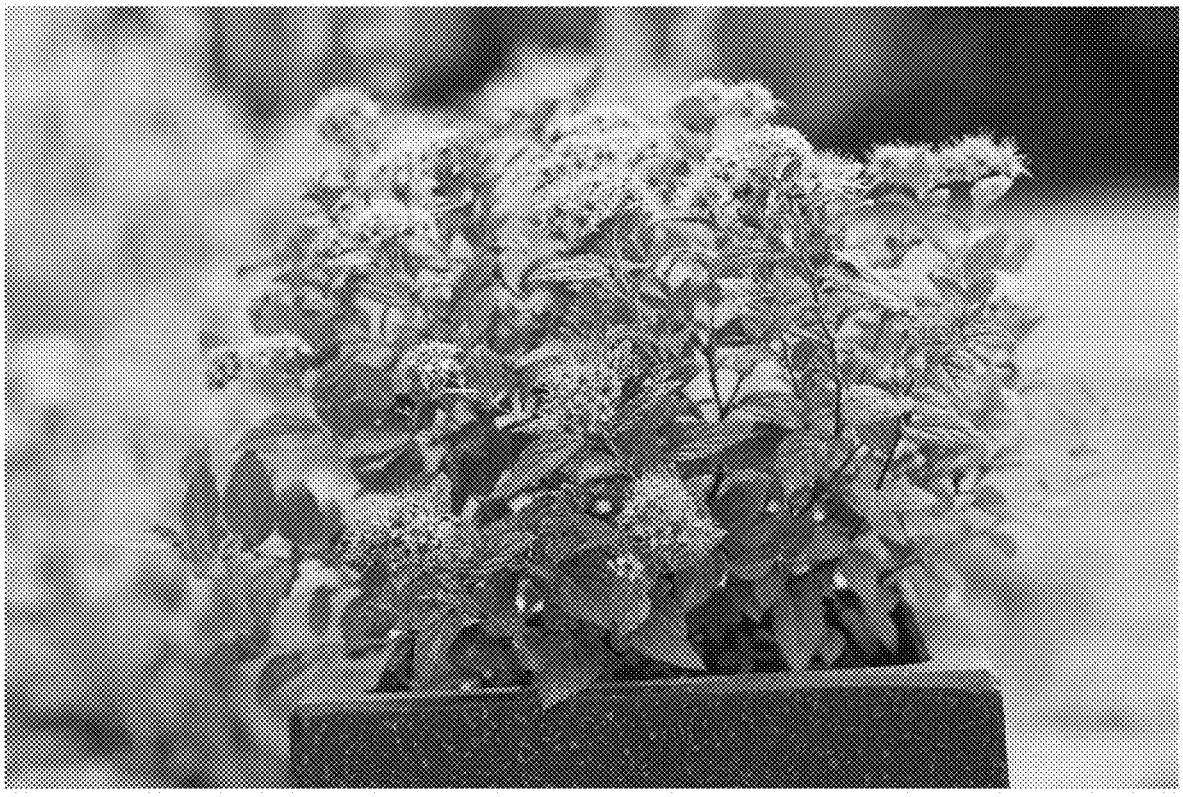
FIG. 3 illustrates a one-year-old plant of 'WALPLUCAR' in its summer foliage. The photo was taken on a one year old plant on Aug. 2, 2022 in Walberton, West Sussex, United Kingdom.

The photographs were made from plants grown out of doors in Walberton, West Sussex, United Kingdom. The illustrated plants had not been pruned or treated with any plant growth regulator. The colors in the drawings are as accurate as possible by conventional photography and may appear different from actual colors due to light reflectance.

BOTANICAL DESCRIPTION OF THE PLANT

The following is a detailed botanical description of the new *Spiraea* cultivar 'WALPLUCAR'. Observations, measurements, values and comparisons were collected in Walberton, West Sussex, United Kingdom from one year old and two years old plants growing in 1 gallon to 3 gallon containers. Plants had received an initial stopping or pinching of the initial rooted cutting upon establishment on its own roots. No growth regulators were used. Plants were grown under typical outdoor conditions of cool, wet spring months and warm, sunny summer months. Color determinations are made in accordance with the 2007 edition of The Royal Horticultural Society Colour Chart of London, England, except where general color terms of ordinary dictionary significance are used. The growing requirements of the new variety are similar to the species.

Botanical classification:

*Genus and species.*—*Spiraea* x *bumalda.*

*Variety.*—'WALPLUCAR'.

*Common name.*—Spiraea.

Parentage:

*Spiraea* 'WALPLUM' (U.S. Plant Pat. No. 29,405).

*Spiraea* 'WALBUMA' (U.S. Plant Pat. No. 9,363).

Propagation:

*Type.*—Internodal stem cuttings rooted in cool greenhouse without chemicals.

*Time to produce a rooted young plant.*—Root initials at 7 days; well-rooted young plants, 4 weeks.

*Root description.*—Prolific branching. Youngest roots fine, diameter 0.25 mm, color RHS 162D.

*Rooting habit.*—Fine and fibrous.

Plant description:

*Plant form.*—Hemispherical dome.

*Plant height.*—50.0 cm.

*Plant diameter or spread.*—50.0 cm.

Branching characteristics:

*Primary branches*—Number of primary branches: 12 to 18. Length of primary branches: 25.0 cm. Diameter of primary branches: 2.0 mm to 3.0 mm. Primary branch strength: Stiff, rigid, woody and brittle with age. Primary branch color: Juvenile growth RHS 153D, mature growth in direct sun RHS N186C. Primary branch texture: Puberulent.

*Lateral branches.*—Number of lateral branches: 3 to 5 lateral branches per primary branch; approximately 175 lateral branches per 2 year old plant. Length of lateral branches: 15.0 cm to 20.0 cm. Diameter of lateral branches: 2.0 mm. Lateral branch strength: Stiff, wiry. Lateral branch color: Juvenile growth RHS 153D, mature growth in direct sun RHS N186C. Lateral branch texture: Puberulent. Number of leaves per lateral branch.—10 to 15.

Internode length: Initially (new growth) 1.4 cm, increasing to 3 cm on two year old plants.

Foliage:

*Leaf.*—Type: Deciduous. Arrangement: Alternate Average length Juvenile, red-colored stage): 2.0 cm. Established mature plants: 5.0 cm. Average width: 2.0 cm Shape of blade: Ovate. Apex: Acute. Base: Cuneate. Attachment: Short petiolate. Margin: Dentate, teeth pointing towards apex. Teeth 1 mm apart on average, depression between teeth 0.5 mm to 1.0 mm. Texture of top surface: Undulating, rugose. Smooth, glossy. Texture of bottom surface: Smooth, matte. Foliage scent: None. Color: Young foliage upper side: RHS N79C. Young foliage under side: RHS N77C. Mature foliage upper side: RHS 137C. Mature foliage under side: RHS 146D. Venation: Type: Pinnate, veins deeply sulcate. Venation color upper side: RHS N77A. Venation color under side: RHS N77C.

Petiole:

*Length.*—3.0 mm.

*Diameter.*—0.75 mm.

*Color.*—RHS 60C.

Flower:

*Bloom period.*—Late May to end of July.

*Natural season.*—June and July.

*Lastingness of blooms.*—14-21 days.

*Flower* (*inflorescence*).—Arrangement: Corymb.

*Inflorescence.*—Diameter: 2.0 cm to 6.0 cm. Height: 3.0 cm 5.0 cm above foliage canopy; occasionally positioned slightly underneath (within) foliage canopy.

Peduncle:

*Length.*13 1.0 cm.

*Diameter.*—1.0 mm to 2.0 mm.

*Color.*—RHS 187A.

*Texture.*—Glabrous, glossy.

*Aspect.*—Upright.

Flowers:

*Number.*—Approximately 30 flowers in each small corymb and 300 flowers in large corymbs.

*Shape*—Rotate.

*Depth.* —2.5 mm.

*Diameter.*—6.0 mm.

*Facing direction.*—Outward or upright.

*Persistent or self-cleaning.*—Self-cleaning.

*Fragrance.*—None.

Petals:

*Shape of petal.*—Ovate.

*Number.*—5.

*Petal arrangement.*—Rotate, unfused.

*Length.*—3.0 mm.

*Width.*—3.0 mm.

*Apex.*—Rounded.

*Petal margin.*—Smooth, entire.

*Petal texture.*—Smooth, glossy.

*Color.*—Upper surface from first opening to maturity: RHS 67B. Under surface from first opening to maturity: RHS 55B. Upper surface at fading: RHS 55D. Under surface at fading: RHS 55D.

Bud:

*Shape.*—Globose.

*Diameter* (*closed, sepals clasping*).—3.0 mm.

*Color.*—RHS 59B.

Calyx/sepals:

*Quantity per flower.*—5, sepals fused at base.

*Shape.*—Lanceolate, longitudinally concave.

*Length.*—3.0 mm.

*Width.*—2 mm.

*Apex.*—Acute.

*Base.*—Truncate.
*Margin.*—Smooth, entire.
*Texture.*—Smooth, semi-glossy.
*Color* (*both surfaces*).—RHS 59A.

Pedicel:
*Length.*—4.0 mm to 5.0 mm.
*Diameter.*—0.5 mm to 1.0 mm.
*Color.*—RHS 187C.
*Texture.*—Glabrous.

Reproductive organs:
*Stamens.*—Number: Numerous, between 12 and 20 per flower. Filament length: 5.0 mm to 8.0 mm. Width: 0.5 mm. Color: RHS 63D.
*Anthers.*—Shape: Ovoid. Length: 2.5 mm, width 1.5 mm. Color: RHS 59A.
*Pollen.*—None observed.
*Pistil.*—Number: 5. Length: 1.0 mm to 2.0 mm.
*Style.*—Length: 1.0 mm to 2.0 mm. Color: RHS 53B.
*Stigma.*—Shape: Globose. Color: RHS 53B.

Pest resistance: Grazed by deer.
Temperature tolerance: USDA Zone 3.
Fruit/seed production: None observed.

COMPARISON WITH PARENTAL AND COMMERCIAL VARIETIES

'WALPLUCAR' is distinguished from the parents as described in Table 1 (please note that the applicant also submits that 'WALBUMA' is also the closest commercial comparison to 'WALPLUCAR').

TABLE 1

Comparison with Parental Varieties

TABLE 1

Comparison with Parental Varieties

| Trait | 'WALPLUCAR' | 'WALBUMA' | 'WALPLUM' |
|---|---|---|---|
| Plant Habit | Dense hemispherical dome | Low growing, spreading | Compact upright |
| Inflor-escence, flower numbers | Corymb of approximately 30-300 flowers | Corymb of 20-200 flowers | Corymb of 20-200 flowers |
| Flowers, first flowering | Dark red-purple | Light red-purple | Dark red-purple |
| Juvenile foliage color, spring, full sun | Purple | Grey-orange | Red |
| Mature foliage color, summer, fall | Green | Yellow-green | Green |

I claim:

1. A new and distinct cultivar of *Spiraea* Plant Named 'WALPLUCAR' as herein illustrated and described.

* * * * *